US010960026B2

(12) United States Patent
Bare et al.

(10) Patent No.: US 10,960,026 B2
(45) Date of Patent: *Mar. 30, 2021

(54) SYSTEMS AND METHODS FOR PREPARING PROTEIN ENHANCED SERUMS

(71) Applicant: ARTHREX, INC., Naples, FL (US)

(72) Inventors: Christopher Bare, Naples, FL (US); Abigail Nabors, Naples, FL (US); Melissa Tucker, Bonita Springs, FL (US); Robert Harrison, Naples, FL (US)

(73) Assignee: ARTHREX, INC., Naples, FL (US)

( * ) Notice: Subject to any disclaimer, the term of this patent is extended or adjusted under 35 U.S.C. 154(b) by 350 days.

This patent is subject to a terminal disclaimer.

(21) Appl. No.: 15/455,474

(22) Filed: Mar. 10, 2017

(65) Prior Publication Data
US 2017/0258849 A1 Sep. 14, 2017

Related U.S. Application Data

(60) Provisional application No. 62/306,297, filed on Mar. 10, 2016.

(51) Int. Cl.
*B01L 3/00* (2006.01)
*B01L 1/00* (2006.01)
*A61K 35/32* (2015.01)

(52) U.S. Cl.
CPC ............ *A61K 35/32* (2013.01); *B01L 3/5021* (2013.01); *B01L 3/50825* (2013.01); *B01L 2200/026* (2013.01); *B01L 2300/041* (2013.01); *B01L 2300/042* (2013.01); *B01L 2300/046* (2013.01); *B01L 2300/047* (2013.01); *B01L 2300/0609* (2013.01); *B01L 2300/0672* (2013.01); *B01L 2300/0832* (2013.01)

(58) Field of Classification Search
CPC ...... B01L 3/50; B01L 3/50853; B01L 3/5082; B01L 2300/042; B01L 2300/047
See application file for complete search history.

(56) References Cited

U.S. PATENT DOCUMENTS 4,257,886 A   3/1981  Kessler
4,904,601 A * 2/1990  Mano ..................... C12M 25/16
                                                          435/295.1

(Continued)

FOREIGN PATENT DOCUMENTS

CA      1040170     10/1978
EP      2687217      1/2014
(Continued)

OTHER PUBLICATIONS

BioPharm Laboratories, LLC "Preparation of Serum from Anticoagulated Blood", Jun. 20, 2012.
(Continued)

*Primary Examiner* — Nathan A Bowers
(74) *Attorney, Agent, or Firm* — DLA Piper LLP US

(57) ABSTRACT

A system for preparing a serum includes a containment device, a cage positioned inside the containment device, a cap attachable to the containment device and configured to cover the cage, an inlet port configured to introduce an autologous fluid into the containment device, and an outlet port configured to remove a serum from the containment device.

21 Claims, 8 Drawing Sheets

(56) References Cited

U.S. PATENT DOCUMENTS

| | | | |
|---|---|---|---|
| 4,921,792 A * | 5/1990 | Trawinski | C12M 27/02 435/394 |
| 5,126,269 A * | 6/1992 | Fike | C12M 27/02 435/297.3 |
| 5,776,336 A | 7/1998 | Holm | |
| 5,998,184 A * | 12/1999 | Shi | C12M 23/08 435/176 |
| 6,099,493 A | 8/2000 | Swisher | |
| 6,416,717 B1 | 7/2002 | Suzuki | |
| 6,503,731 B2 | 1/2003 | Marx | |
| 6,558,341 B1 | 5/2003 | Swisher | |
| 6,713,246 B1 | 3/2004 | Reinecke et al. | |
| 6,719,901 B2 | 4/2004 | Dolecek | |
| 6,905,612 B2 | 6/2005 | Dorian | |
| 7,025,212 B2 | 4/2006 | Amano | |
| 7,553,413 B2 | 6/2009 | Dorian | |
| 8,177,072 B2 | 5/2012 | Chapman | |
| 8,187,475 B2 | 5/2012 | Hecker | |
| 8,419,705 B2 | 4/2013 | Omori | |
| 8,460,227 B2 | 6/2013 | Bare et al. | |
| 8,506,823 B2 | 8/2013 | Chapman | |
| 8,511,479 B2 | 8/2013 | Chapman | |
| 8,511,480 B2 | 8/2013 | Chapman | |
| 8,586,324 B2 | 11/2013 | Leach | |
| 8,603,345 B2 | 12/2013 | Ross et al. | |
| 8,753,690 B2 | 6/2014 | Higgins et al. | |
| 8,783,470 B2 | 7/2014 | Hecker | |
| 8,796,017 B2 | 8/2014 | Suzuki | |
| 9,011,687 B2 | 4/2015 | Swift | |
| 9,011,846 B2 | 4/2015 | Overholser | |
| 9,119,829 B2 | 9/2015 | Higgins et al. | |
| 9,205,110 B2 | 12/2015 | Bare | |
| 9,480,730 B2 | 11/2016 | Chapman | |
| 9,629,798 B2 | 4/2017 | Senderoff | |
| 9,815,038 B2 | 11/2017 | Leach | |
| 2001/0015338 A1 | 8/2001 | Nanba | |
| 2002/0065047 A1 | 5/2002 | Moose | |
| 2003/0010718 A1 | 1/2003 | Burbank | |
| 2004/0120942 A1 | 6/2004 | McGinnis | |
| 2005/0271646 A1 | 12/2005 | Delmotte | |
| 2006/0134094 A2 | 6/2006 | Delmotte | |
| 2006/0278588 A1 | 12/2006 | Woodell-May | |
| 2008/0020049 A1 | 1/2008 | Darling | |
| 2008/0047908 A1 | 2/2008 | Sekine | |
| 2008/0220462 A1 | 9/2008 | Bell et al. | |
| 2008/0267940 A1 | 10/2008 | Mohammed | |
| 2008/0274496 A1 * | 11/2008 | Duymelinck | B01L 3/508 435/40.52 |
| 2009/0105611 A1 | 4/2009 | Wilkinson et al. | |
| 2009/0148941 A1 * | 6/2009 | Florez | C12M 23/08 435/325 |
| 2009/0152744 A1 * | 6/2009 | Mou | B01F 7/1625 261/84 |
| 2011/0183406 A1 * | 7/2011 | Kensy | A61M 1/0001 435/283.1 |
| 2012/0115181 A1 * | 5/2012 | Al-Rasheed | C12M 23/08 435/34 |
| 2013/0178425 A1 | 7/2013 | Higgins et al. | |
| 2014/0249071 A1 | 9/2014 | Bare et al. | |
| 2014/0271870 A1 | 9/2014 | O'Shaughnessey et al. | |
| 2014/0274895 A1 | 9/2014 | Binder et al. | |
| 2014/0319081 A1 | 10/2014 | Davey | |
| 2015/0182202 A1 | 7/2015 | Wan | |
| 2015/0182603 A1 | 7/2015 | Chapman | |
| 2016/0106117 A1 * | 4/2016 | Gazenko | A23C 9/122 435/304.1 |
| 2017/0027822 A1 * | 2/2017 | Margolin | A23C 29/06 |
| 2017/0087228 A1 | 3/2017 | Turzi | |
| 2017/0189537 A1 | 7/2017 | Senderoff | |
| 2017/0258877 A1 | 9/2017 | Bare | |
| 2017/0336424 A1 | 11/2017 | Rida | |
| 2017/0361317 A1 | 12/2017 | Wilkinson | |
| 2018/0015147 A1 | 1/2018 | Bouckenooghe | |
| 2018/0110917 A1 | 4/2018 | Turzi | |

FOREIGN PATENT DOCUMENTS

| | | |
|---|---|---|
| GB | 2433219 A | 6/2007 |
| WO | 2007014742 | 2/2007 |
| WO | 2014149301 A1 | 9/2014 |
| WO | 2017/156375 A1 | 9/2017 |

OTHER PUBLICATIONS

Clotalyst, Autologous Activation Solution (2012).
Office Action for U.S. Appl. No. 15/455,417, dated Nov. 5, 2018, 30 pages.
Office Action for U.S. Appl. No. 15/455,417, dated May 24, 2018, 35 pages.
International Preliminary Report on Patentability for corresponding PCT application No. PCT/US2017/021751, dated Sep. 11, 2018.
The International Search Report and Written Opinion for PCT Application No. PCT/US2017/021757, dated Jul. 19, 2018.
International Preliminary Report on Patentability for Application No. PCT/US2017/021757 dated Sep. 20, 2018.
The Partial International Search for International Application No. PCT/US2017/021757, dated Jun. 14, 2017.
U.S. Appl. No. 15/455,417, Office Action dated Mar. 19, 2019, 18 pages.

* cited by examiner

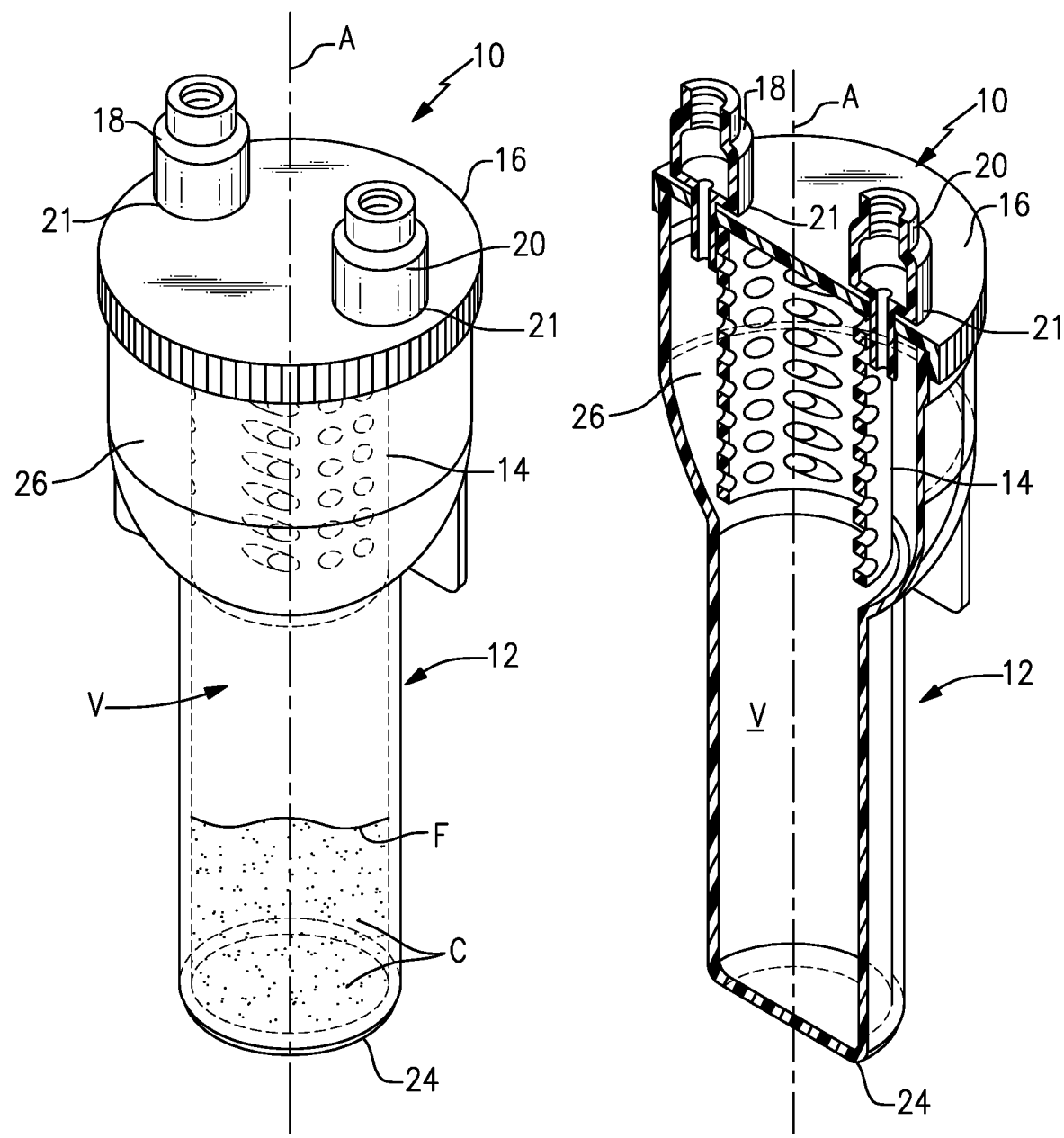

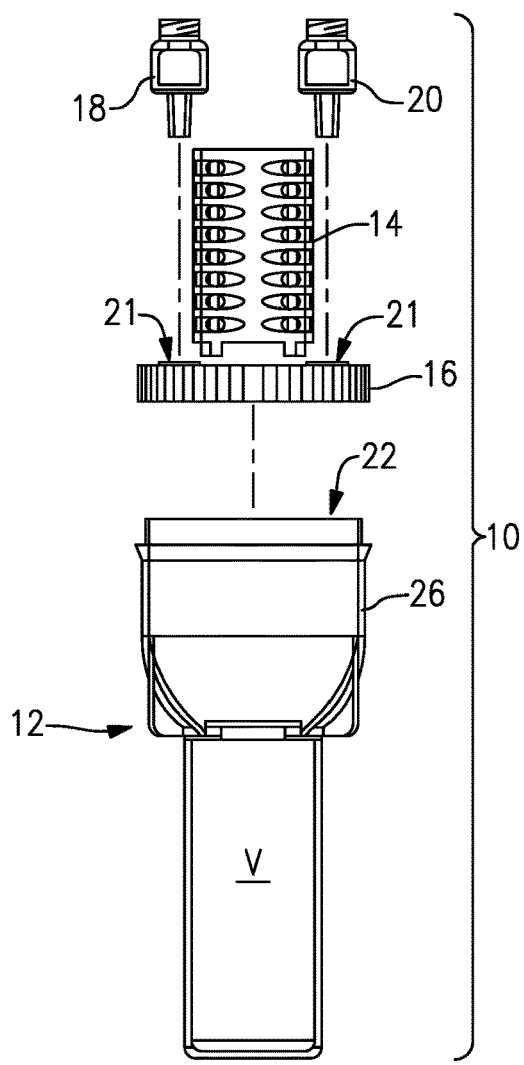
FIG.3
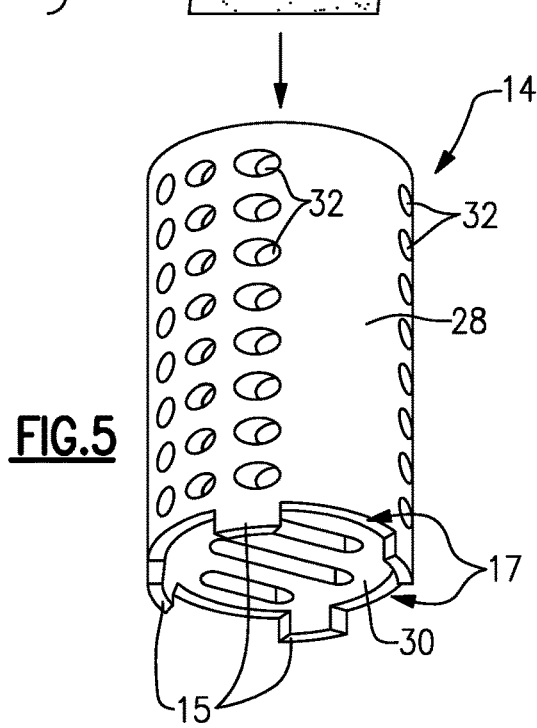
FIG.4
FIG.5

SYSTEMS AND METHODS FOR PREPARING PROTEIN ENHANCED SERUMS

CROSS-REFERENCE TO RELATED APPLICATIONS

This disclosure claims priority to U.S. Provisional Application No. 62/306,297, filed on Mar. 10, 2016, the entirety of which is incorporated herein by reference.

BACKGROUND

This disclosure relates to systems and methods for preparing a protein enhanced serum.

Healing injuries involve a complex series of events in which proteins in the blood including growth factors are released. The release of growth factors signals the healing process to begin. Many growth factors are derived from platelets. Increased growth factor levels improve the recruitment of cells to an injury site and optimize the environment for healing. Accordingly, autologous blood components that are derived from a subject, such as platelet-rich plasma (PRP), have been used in various surgical procedures to provide a concentrated level of growth factors at the point of care.

SUMMARY

This disclosure describes systems and methods for preparing a protein enhanced serum. A protein enhanced serum can be used to treat tissue injuries at the point of care in either human or non-human subjects.

An exemplary system for preparing a protein enhanced serum includes a containment device configured to receive both cartilage and an autologous fluid. The autologous fluid interacts with the cartilage inside the containment device to promote the production of anabolic growth factors within the autologous fluid. A protein enhanced serum can be harvested from the autologous fluid for treating injuries.

A system for preparing a serum according to an exemplary aspect of the present disclosure includes, inter alia, a containment device, a cage positioned inside the containment device, a cap attachable to the containment device and configured to cover the cage, an inlet port configured to introduce an autologous fluid into the containment device, and an outlet port configured to remove a serum from the containment device. The cage is positioned to substantially prevent clogging of the outlet port as the serum is removed.

A method for preparing a serum according to another exemplary aspect of the present disclosure includes, inter alia, contacting an autologous fluid to cartilage inside a containment device. The containment device includes a cage housed therein and configured to hold the cartilage. The method includes incubating the containment device and centrifuging the containment device to separate a serum from the autologous fluid.

BRIEF DESCRIPTION OF THE DRAWINGS

FIG. 1 illustrates a system for preparing a protein enhanced serum.

FIG. 2 illustrates a cross-sectional view of the system of FIG. 1.

FIG. 3 illustrates an exploded view of the system of FIG. 1.

FIG. 4 illustrates a cage of the system of FIG. 1 according to a first embodiment of this disclosure.

FIG. 5 illustrates a cage of the system of FIG. 1 according to a second embodiment of this disclosure.

DETAILED DESCRIPTION

Figure 6A:
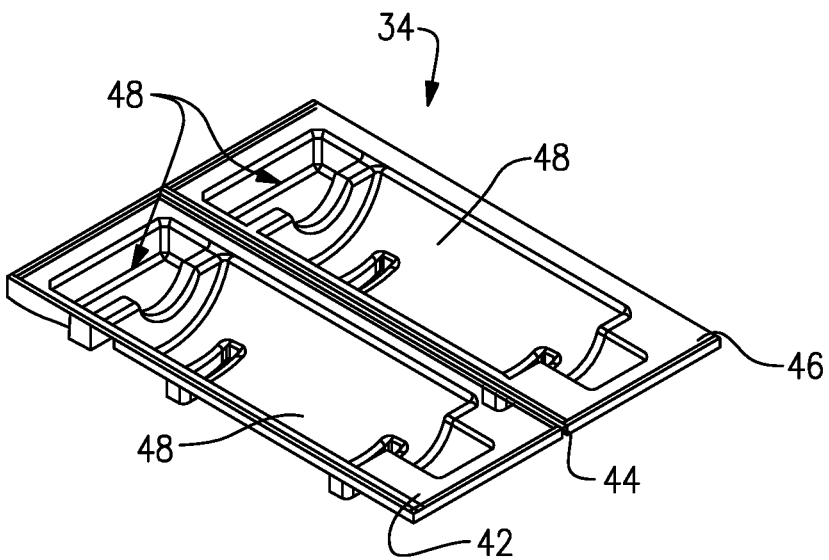
FIGS. 6A and 6B illustrate a tray assembly for packaging a system for preparing a protein enhanced serum.

This disclosure describes systems and methods for preparing a protein enhanced serum. Once prepared, a protein enhanced serum can be used to treat an injury at the point of care of a subject.

In some embodiments, a system for preparing a protein enhanced serum includes a containment device configured to hold both cartilage and an autologous fluid. The autologous fluid can interact with the cartilage inside the containment device to simulate a tissue injury. Simulating a tissue injury in this manner promotes the production of anabolic growth factors within the autologous fluid. These and other features are discussed in greater detail in the following paragraphs of this detailed description.

A system for preparing a serum according to an exemplary aspect of the present disclosure includes, inter alia, a containment device, a cage positioned inside the containment device, a cap attachable to the containment device and configured to cover the cage, an inlet port configured to introduce an autologous fluid into the containment device, and an outlet port configured to remove a serum from the containment device. The cage is positioned to substantially prevent clogging of the outlet port as the serum is removed.

In an embodiment, a containment device of a system for preparing a serum is a test tube having a closed distal end.

In another embodiment, a cage of a system for preparing a serum is a hollow cylinder.

In another embodiment, a cage of a system for preparing a serum includes a cylindrical body having a floor and is configured to receive cartilage.

In another embodiment, a tray assembly includes a receptacle for receiving a containment device of a system for preparing a serum.

In another embodiment, a tray assembly is configured to house at least a containment device, a needle, and a syringe of a system for preparing a serum.

In another embodiment, a hand warmer is packaged inside a tray assembly along with a containment device of a system for preparing a serum.

In another embodiment, a tray assembly includes a first housing connected to a second housing by a hinge.

In another embodiment, a syringe is connectable to an inlet port to introduce an autologous fluid into a containment device of a system for preparing a serum. The syringe is connectable to an outlet port to remove the serum from the containment device.

In another embodiment, a cage is removable from a containment device of a system for preparing a serum.

A method for preparing a serum according to another exemplary aspect of the present disclosure includes, inter alia, contacting an autologous fluid to cartilage inside a containment device. The containment device includes a cage housed therein and configured to hold the cartilage. The method includes incubating the containment device and centrifuging the containment device to separate a serum from the autologous fluid.

In an embodiment, a method for preparing a serum includes contacting an autologous fluid to cartilage to produce anabolic growth factors in the autologous fluid.

In another embodiment, a cartilage used during a method of preparing a serum includes allograftic cartilage, autologous cartilage, or both.

In another embodiment, a method for preparing a serum includes positioning cartilage within a cage prior to contacting an autologous fluid to the cartilage.

In another embodiment, a method for preparing a serum includes removing cartilage from a containment device after incubating the containment device but prior to centrifuging the containment device.

In another embodiment, a method for preparing a serum includes using cartilage, which has soaked in a serum inside a containment device, to treat a subject.

In another embodiment, a method for preparing a serum includes incubating a containment device within a tray assembly by activating a hand warmer.

In another embodiment, a method for preparing a serum includes adding a bone marrow product to a containment device after incubating the containment device.

In another embodiment, a method for preparing a serum includes removing waste from a protein enhanced serum using a concentrator assembly.

In another embodiment, a method for preparing a serum includes extracting the serum from a containment device, and administering the serum at a point of care of a subject.

FIGS. 1, 2 and 3 illustrate a system 10 for preparing a protein enhanced serum. The protein enhanced serums described in this disclosure may be a fluid or composition that includes growth factors, cytokines, other prophylactically or therapeutically active agents, or combinations thereof. For example, the protein enhanced serums of this disclosure could include interleukin (IL)-1 receptor antagonist (IL-1Ra), IL-4, IL-6, IL-10, IL-11, IL-13, interferon (IFN)-α, tumor necrosis factor (TNF)-α, platelet derived growth factor (PDGF), granulocyte-colony stimulating factor (G-CSF), transforming growth factor (TGF)-β, insulin-like growth factor (IGF-1), fibroblastic growth factor (bFGF), vascular endothelial growth factor (VEGF), and/or alpha 2-macroglobulin (A2M), among various other therapeutically active agents. In an embodiment, a protein enhanced serum includes growth factors, cytokines, or therapeautically active agents, or combinations thereof, in levels greater than basal levels. In an embodiment, a protein enhanced serum includes a decreased level of IL-1β compared to a basal level.

The exemplary system 10 may include a containment device 12, a cage 14, a cap 16, an inlet port 18 and an outlet port 20. In a non-limiting embodiment, the containment device 12 is configured as a test tube. However, containment devices having other sizes, shapes and configurations are also contemplated within the scope of this disclosure. In another non-limiting embodiment, the containment device 12 is made of a sterilizable material, such as any suitable glass, ceramic or plastic material. In yet another non-limiting embodiment, the containment device 12 is made of a transparent material for visualizing the contents of the containment device 12 during its use.

The containment device 12 extends along a longitudinal axis A between a proximal opening 22 (best illustrated in FIG. 3) and a closed distal end 24. An internal volume V of the containment device 12 is configured to hold both cartilage C and an autologous fluid F (see FIG. 1), as discussed in greater detail below. The cartilage C may include allograftic cartilage, autologous cartilage, or both. The autologous fluid F may include blood such as whole blood; platelet-rich plasma (PRP), e.g., autologous conditioned plasma (Arthrex ACP®); platelet-poor plasma (PPP); bone marrow aspirate (BMA); bone marrow concentrate (BMC); stem cells (e.g., mesenchymal stem cells), or any combinations of these fluids.

The cap 16 may be removably attached to the containment device 12 to cover the proximal opening 22 and therefore selectively conceal the contents of the containment device 12. In a non-limiting embodiment, the cap 16 is threadably attached to the containment device 12. In another non-limiting embodiment, the cap 16 is press-fit onto the containment device 12. Other containment device-to-cap connections are also contemplated within the scope of this disclosure.

The inlet port 18 and the outlet port 20 are received through openings 21 formed in the cap 16. In a non-limiting embodiment, the inlet port 18 and the outlet port 20 are luer-type connectors adapted for lockingly engaging a tip of a syringe (syringe not shown in FIG. 1, 2 or 3). The inlet port 18 may be used to deliver the autologous fluid F into the internal volume V of the containment device 12. The outlet port 20 may be used to remove a protein enhanced serum from the containment device 12 after the autologous fluid F has been exposed to and has interacted with the cartilage C to produce anabolic growth factors. The anabolic growth factors will separate from and float in the surrounding fluid and can be retrieved through the outlet port 20 for subsequent delivery at an injured tissue site or point of care. The inlet port 18 and the outlet port 20 are swabbable valves, in another non-limiting embodiment.

Referring now to FIGS. 1-5, the cage 14 is positioned inside the containment device 12. The cage 14 can be used to hold the cartilage C and/or prevent clogging of the inlet port 18 and the outlet port 20. In other words, the cage 14 can act as a filter to prevent clogging. In a non-limiting embodiment, the cage 14 is positioned within a flared portion 26 of the containment device 12. The flared portion 26 is proximate to the proximal opening 22. The cage 14 may be either securely affixed (e.g., welded, etc.) inside the containment device 12 or removable from the containment device 12. The cage 14 may include legs 15 that aid to position and/or secure the cage 14 inside the containment device 12. Slots 17 extend between the legs 15. The cage 14 can include any number of legs 15 and slots 17.

The cage 14 may include a cylindrical body 28, although other shapes are also contemplated within the scope of this disclosure. In a first non-limiting embodiment, the cylindrical body 28 is a hollow cylinder that includes an open top and bottom (see FIG. 4). In another non-limiting embodiment the cylindrical body 28 includes a floor 30 (see FIG. 5) such that cartilage C can be loaded into the cage 14 and prevented from escaping into the internal volume V of the containment device 12. Thus, in some embodiments, the cage 14 is configured to hold the cartilage C inside the containment device 12.

A plurality of openings 32 may extend through the cylindrical body 28 of the cage 14. Once introduced into the containment device 12, the autologous fluid F may pass through the openings 32 and be exposed to the cartilage C that is either housed inside the cage 14 or elsewhere within the containment device 12. Exposure to the cartilage C causes the cells within the autologous fluid F to function as if a tissue injury has occurred. Stated another way, the autologous fluid F and the cartilage C interact to "simulate" a tissue injury. The cells of the autologous fluid F thus release anabolic growth factors which can be harvested from the autologous fluid F and used to treat a subject at the point of care.

Figure 6B:
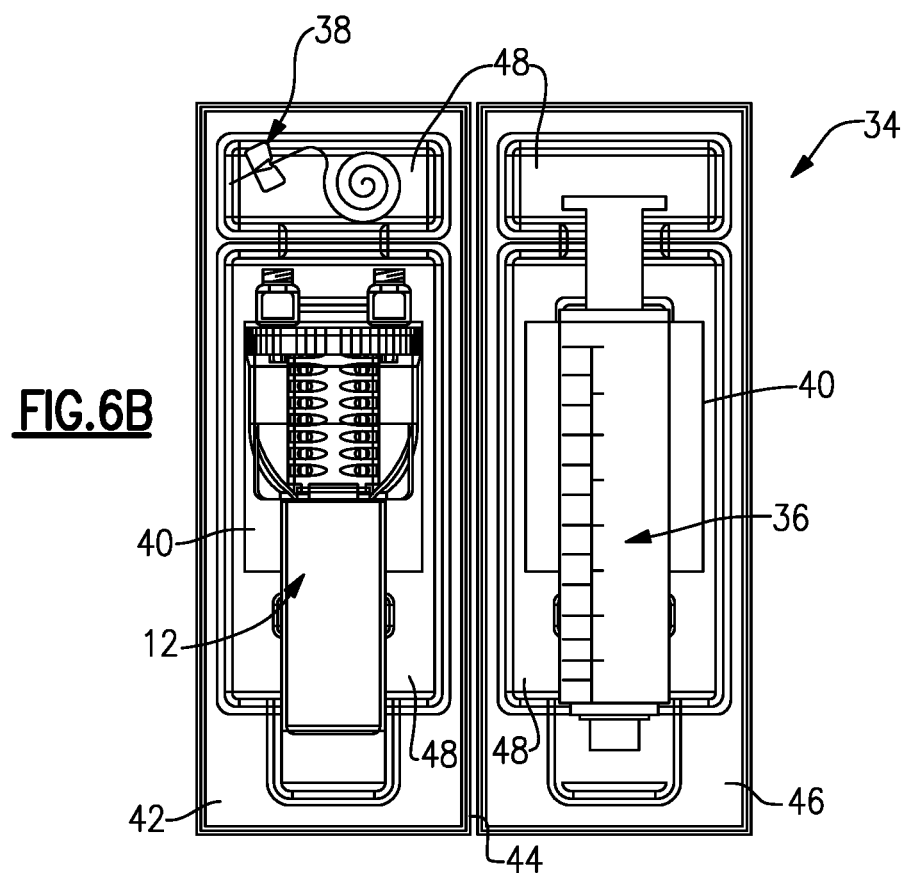

FIGS. 6A and 6B illustrate an exemplary tray assembly 34 for conveniently packaging the various components of the system 10. For example, the tray assembly 34 may package the containment device 12, a syringe 36, a needle 38, and hand warmers 40 of the system 10. In a first non-limiting embodiment, the tray assembly 34 includes a first housing 42 that is connected to a second housing 46 along a hinge 44. The first housing 42 is foldable about the hinge 44 to a position over top of the second housing 46 to enclose the system 10. In another non-limiting embodiment, the first housing 42 is separate from and connectable to the second housing 46, such as by using a snap-fit or interference connection. Each housing 42, 46 includes one or more receptacles 48 for receiving the containment device 12, the syringe 36, the needle 38, the hand warmers 40 and/or any other component of the system 10. The first and second housings 42, 46 may be made of an insulating material.

In another non-limiting embodiment, the tray assembly 34 is employable as a portable incubator. For example, after loading the autologous fluid F and the cartilage C into the containment device 12, the hand warmers 40 are activated in a known manner and the containment device 12 is placed inside the tray assembly 34 along with the activated hand warmers 40. In a non-limiting embodiment, each hand warmer 40 is positioned within one of the receptacles 48 such that it is between the tray assembly 34 and the containment device 12. The tray assembly 34 is then concealed by connecting the first housing 42 to the second housing 46. The hand warmers 40 release heat that augments interaction/incubation between the autologous fluid F and the cartilage C, thus promoting the production of a protein enhanced serum within the autologous fluid F. The protein enhanced serum can be extracted from the containment device 12 using the syringe 36 and can then be administered at the point of care.

FIGS. 7-14, with continued reference to FIGS. 1-6B, schematically illustrate an exemplary method for preparing a protein enhanced serum. These figures illustrate, in sequential order, a non-limiting embodiment for preparing a protein enhanced serum that is subsequently used to treat a tissue injury of a human or non-human subject. It should be understood; however, that fewer or additional steps than are recited below could be performed and that the recited order of steps is not intended to limit this disclosure.

Figure 7:
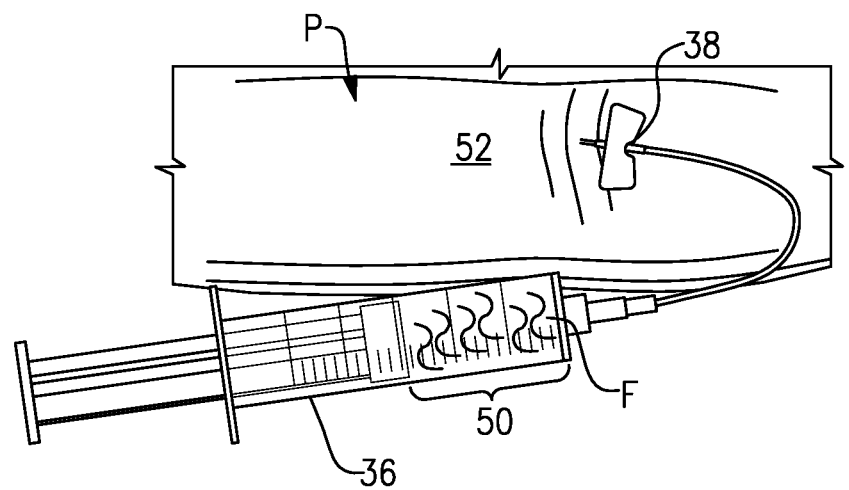
FIG. 7 schematically illustrates harvesting an autologous fluid sample from a subject.

Referring first to FIG. 7, a sample 50 of autologous fluid F may be harvested from a body 52 of a subject P. The sample 50 may be harvested from whole blood (e.g., venous) of the subject P or from a bone of the subject P. In a non-limiting embodiment, the sample 50 is collected using the syringe 36 and the needle 38 of the system 10.

Figures 8A, 8B:
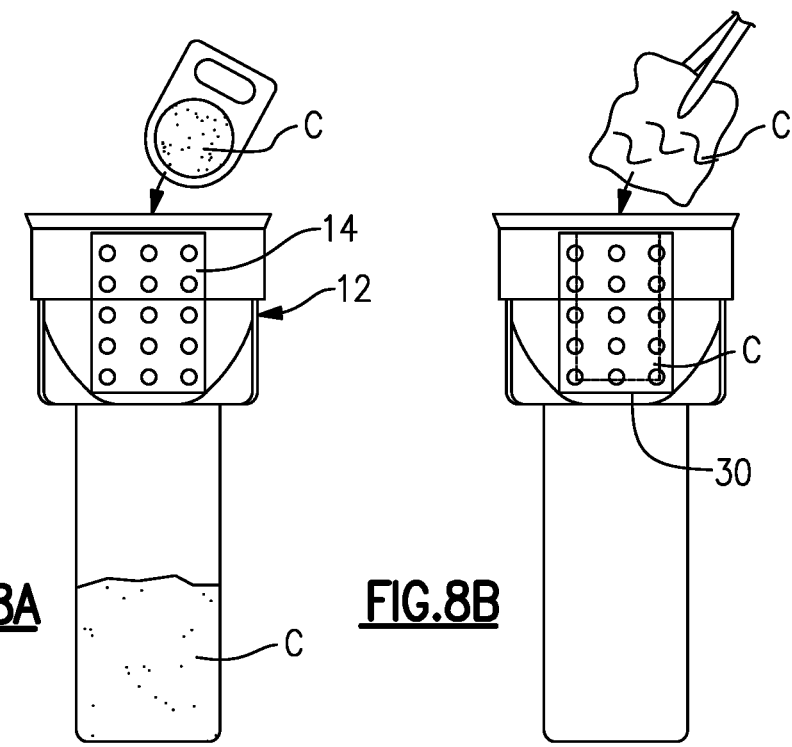
FIGS. 8A and 8B schematically illustrate loading cartilage into a containment device of a system for preparing a protein enhanced serum.

Next, as shown in FIGS. 8A and 8B, cartilage C may be loaded into the containment device 12 of the system 10. In a first non-limiting embodiment, the cartilage C accumulates toward the closed distal end 24 of the containment device 12 (see, for example, FIG. 8A). This may occur if the cage 14 of the system 10 is a hollow cylinder like that shown in FIG. 4. In another non-limiting embodiment, the cartilage C is held within the cage 14 (see FIG. 8B). This may occur if the cage 14 of the system 10 includes the floor 30 like that shown in FIG. 5.

Figure 9:
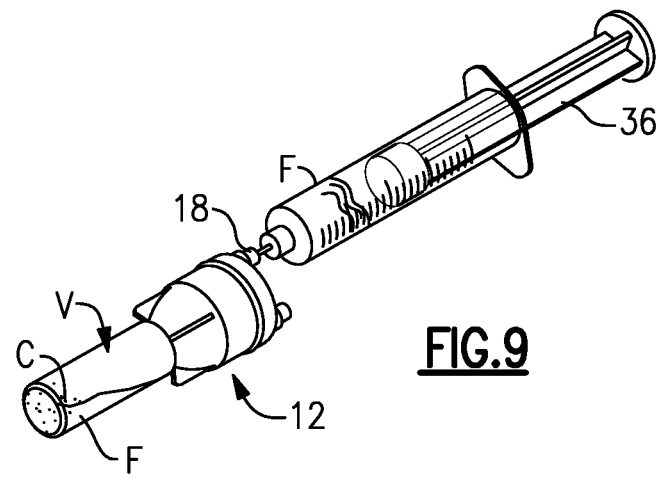
FIG. 9 schematically illustrates introducing an autologous fluid into the containment device shown in FIG. 8.

Referring now to FIG. 9, the autologous fluid F is introduced into the containment device 12. The sample 50 of the autologous fluid F may include whole blood, platelet-rich plasma (PRP), e.g., ACP, platelet-poor plasma (PPP), bone marrow aspirate (BMA), bone marrow concentrate (BMC), stem cells or any combinations of such fluids. Various preparation techniques may optionally be performed on the sample 50 to prepare a customized platelet formulation prior to introducing the autologous fluid F into the containment device 12. In a non-limiting embodiment, the autologous fluid F is introduced into the containment device 12 by connecting the syringe 36 to the inlet port 18 and then injecting the autologous fluid F into the internal volume V of the containment device 12.

The cartilage C and the autologous fluid F are exposed to one another inside the containment device 12. The cartilage C and the autologous fluid F are exposed to one another by introducing the autologous fluid F into the containment device 12 so it contacts the cartilage C. This exposure simulates a tissue injury and therefore causes the cells within the autologous fluid F to begin to release anabolic growth factors.

Figure 10:
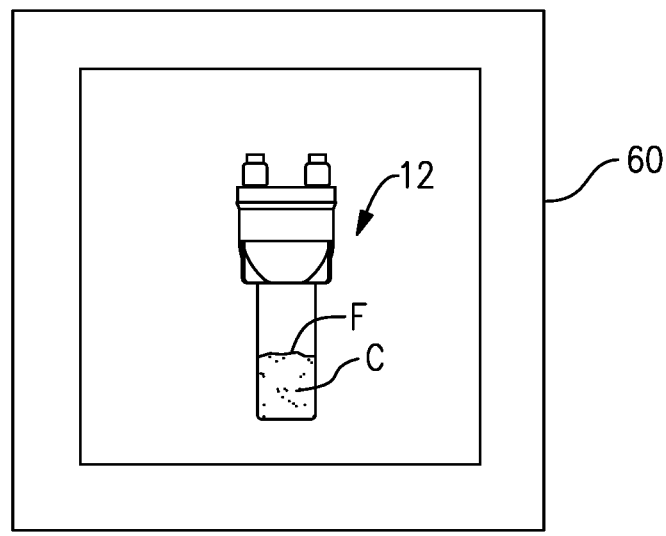
FIG. 10 schematically illustrates incubating the containment device of the system for preparing a protein enhanced serum.

The containment device 12 may next be incubated within an incubation device 60 as schematically shown in FIG. 10. The incubation device 60 could be any known incubator. In a non-limiting embodiment, the incubation device 60 is the tray assembly 34 of the system 10 (see FIGS. 6A and 6B). The tray assembly 34 and the hand warmers 40 provide a portable incubation device. The containment device 12 may be incubated for a suitable amount of time at a suitable temperature to augment the release of anabolic growth factors within the autologous fluid F. In a non-limiting embodiment, the containment device 12 is incubated for between 30 minutes and 24 hours at ambient conditions. In another non-limiting embodiment, the containment device 12 is incubated at a temperature between 35 and 39 degrees Celsius (95 to 102.2 degrees Fahrenheit).

If the cage 14 with the floor 30 of FIG. 5 is used with the system 10, the cage 14 may optionally be removed from the containment device 12 after incubation. The cap 16 is removed from the containment device 12 to access the cage 14. The cartilage C may then be removed from the cage 14. The cartilage C, which has been advantageously soaked in a protein enhanced serum, may optionally be delivered back to the subject at the point of care. In this way, the system 10 can be used to produce two products: the protein enhanced serum and a serum enhanced cartilage product.

In another optional embodiment, a bone marrow product such as BMA or BMC may be added to the containment device 12 after incubation for interaction with the autologous fluid F. The bone marrow product adds mesenchymal stem cells for proliferation and differentiation into chondrocytes. This embodiment will allow the ability to not only deliver an enhanced serum of proteins/cytokines; but active progenitor cells could be delivered after being exposed to the serum within the containment device 12. Autologous stem cells (hematopoetic and/or mesenchymal) would be exposed to autologous proteins and allow for proliferation and/or differentiation.

Figure 11:
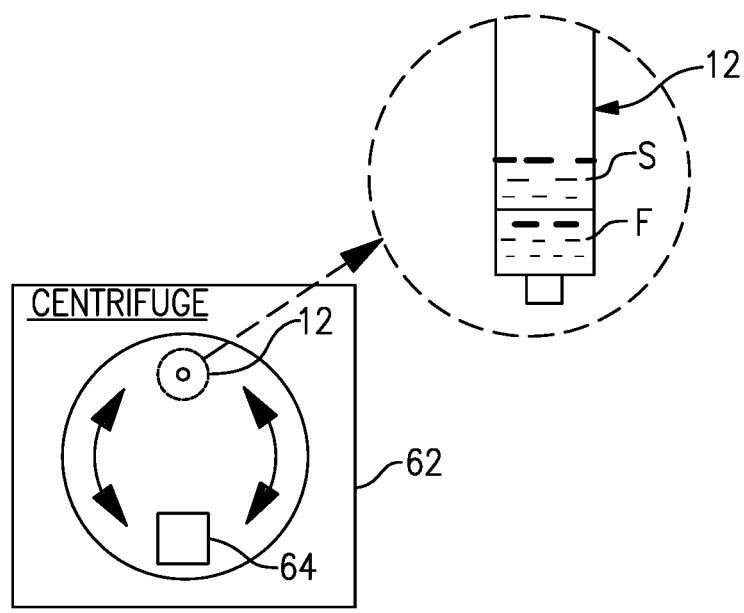
FIG. 11 schematically illustrates separation of the protein enhanced serum from the autologous fluid.
Figure 12:
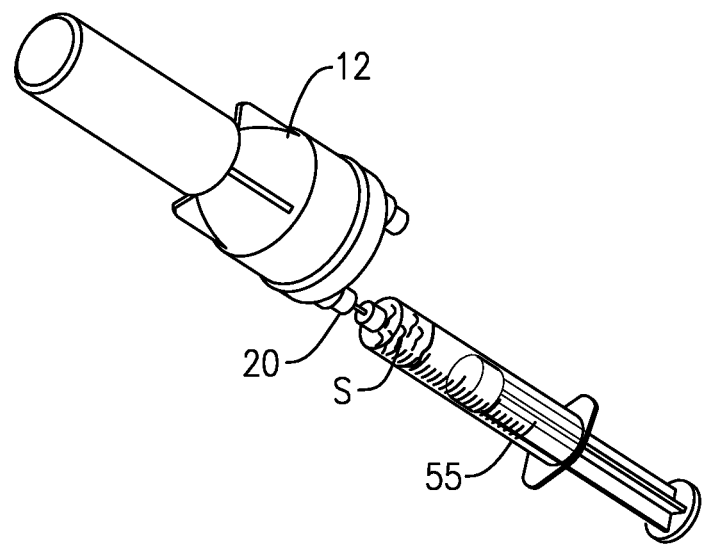
FIG. 12 schematically illustrates removing a protein enhanced serum from a containment device.

FIG. 11 schematically illustrates centrifuging the containment device 12, which includes the autologous fluid F and optionally the cartilage C and/or the bone marrow product. The hard spinning associated with the centrifuging process causes a protein enhanced serum S to separate from and "float" on top of the autologous fluid F. This separation can be achieved using a centrifuge 62 (shown schematically) or by using other known separating techniques. In a non-limiting embodiment, the containment device 12 and an appropriate counterbalance 64 are inserted into the centrifuge 62 and then spun at approximately 2700×g/1500 RPM for around five minutes to separate the protein enhanced serum S from the autologous fluid F. Once adequately separated, the protein enhanced serum S can be extracted through the outlet port 20 of the containment device 12 by attaching another syringe 55 to the outlet port 20 and actuating a plunger of the syringe 55 (see FIG. 12).

Figure 13:
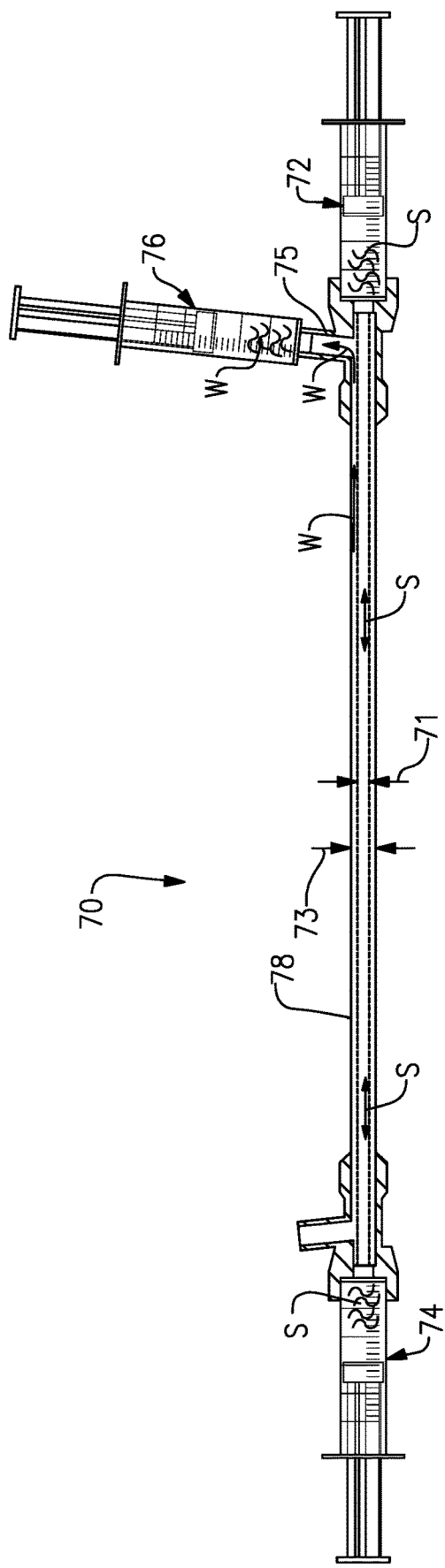
FIG. 13 schematically illustrates the use of a concentrator assembly for removing waste from a protein enhanced serum.

Prior to removing the protein enhanced serum S from the containment device 12, a concentrator assembly 70 may optionally be used to remove water or waste from the protein enhanced serum S. This is schematically illustrated in FIG. 13. The concentrator assembly 70 includes a first syringe 72, a second syringe 74, a waste collection syringe 76 and tubing 78 that connects between the first syringe 72 and the second syringe 74. Protein enhanced serum S is communicated in the tubing 78 between the first syringe 72 and the second syringe 74. The tubing 78 includes an inner portion 71 and an outer portion 73. Waste W, such as water, is released into the outer portion 73, which acts as a filter, as the protein enhanced serum 73 is passed back and forth through the inner portion 71 of the tubing 78. The waste W is collected through a port 75 into the waste collection syringe 76 and can then be discarded. Removal of water and other waste renders a serum S that is more concentrated with proteins.

Figure 14:
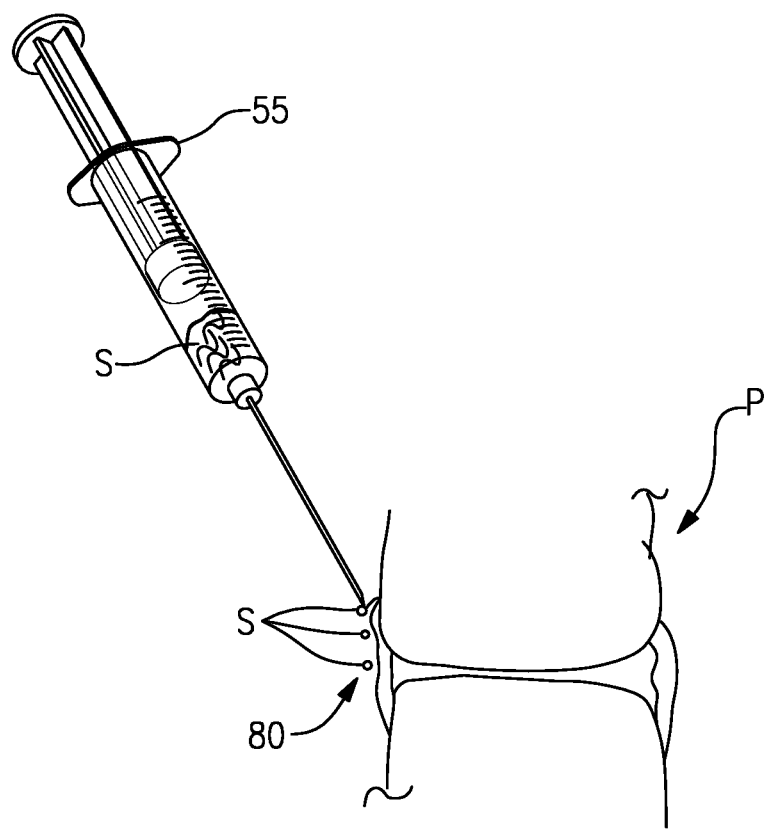
FIG. 14 schematically illustrates application of a protein enhanced serum at the point of care of a subject.

Finally, as shown schematically at FIG. 14, the protein enhanced serum S may be applied to a tissue injury 80 of a subject P. The syringe 55 or some other device may be used to administer the protein enhanced serum S at the point of care. If necessary or desired, the protein enhanced serum S can be divided into multiple doses and then stored in suitable containers for later use for treating a diseased condition (e.g., osteoarthritis, tendonitis, bursitis, epicondylitis, myositis, carpal tunnel, etc.).

EXAMPLES

Example 1

Blood Flow for Cage with Two or Four Slots

A cage 14 having two slots 17 and a cage 14 having four slots 17 were tested for blood flow in the containment devices 12. The method was also tested for effects on cell counts.
Methods Containment devices 12 as exemplified herein were fitted with a cage 14 having (2) slots 17 or (4) slots 17. 60 mL of whole blood (without anticoagulants) were injected into the inlet port 18 of a containment device 12. The containment devices 12 contained 0.425 oz of uncoated 3 mm borosilicate spheres. The containment device was gently inverted 10 times followed by a 24 hr incubation at 37° C. Following the incubation, the containment device 12 was placed in an Arthrex ACP® centrifuge bucket and centrifuged for 10 minutes at 4000 rpm. A syringe was connected to the outlet port 20, and the serum was withdrawn. The serum collection was stopped when the clot began to approach the outlet port 20. The samples were not filtered or filtered through a 0.2 μm hydrophilic filter, a 5 μm hydrophilic filter, or a 5 μm hydrophobic filter. Complete blood counts were measured on a XE-5000 Hematology Analyzer (Sysmex Corp., Hialeah, Fla.).
Results There was no difference in blood flow through the cage 14 in the containment device between a two slot cage 14 and a four slot cage 14.

Filtration, filter size, and hydrophilicity or hydrophobicity did not affect the cell counts of the serum.

Example 2

Activator Testing

Various activators were tested in the containment device 12 to measure IL-1Ra and IL-1β levels in the enhanced serum.
Methods A phlebotomist drew whole blood from three subjects into a 60 mL syringe. Donor whole blood was then injected into a 15 mL Blue Max Jr. centrifuge tube (Becton Dickinson, East Rutherford, N.J.) containing 3 mL of a borosilicate product (Mo-Sci Corp., Rolla, Mo.), one unit of collagen (DSM, Exton, Pa.), or a 1×1 cc volume of BioCartilage® lyophilized powder (Arthrex, Naples, Fla.). The total volume of the tube (whole blood plus activator) equaled 15 mL. Ten different borosilicate products were tested. Each tube was gently inverted five times and then incubated at 37° C. for 24 hours.

After 24 hours, the tubes were removed from the incubator and centrifuged for 10 minutes at 4000 rpm in a Hettich® swing bucket centrifuge (Beverly, Mass.). After 10 minutes, the tubes were kept in an upright position and placed in a test tube rack in an upright position. All of the serum was withdrawn from each upright tube with a 10 mL syringe without a filter. The serum was tested for IL-1Ra and IL-1β levels via an ELISA.
Results The IL-1Ra and IL-1β levels were averaged from testing each of the three donors (Table 1). The IL-1Ra to IL-1β ratio was calculated for each donor and then averaged to produce the average IL-1Ra to IL-1β ratio. Almost all of the borosilicate products produced a similar IL-1Ra to IL-1β ratio. However, the 74 μm borosilicate sphere had a much higher IL-1Ra to IL-1β ratio. The IL-1Ra to IL-1β ratio for collagen was similar to most of the borosilicate products. Using BioCartilage® as the activator produced the largest IL-1Ra to IL-1β ratio.

TABLE 1

| Activator | IL-1Ra (pg/mL) | IL-1β (pg/mL) | Average IL-1Ra/IL-1β |
|---|---|---|---|
| 5 mm frit | 13211 | 244 | 61 |
| 5 mm sphere | 18362 | 237 | 76 |
| 3 mm sphere hyaluronic acid coated | 8198 | 95 | 105 |
| 3 mm sphere | 21035 | 393 | 74 |
| 3 mm frit silane coated | 20711 | 645 | 32 |
| 3 mm frit | 16762 | 280 | 69 |

TABLE 1-continued

| Activator | IL-1Ra (pg/mL) | IL-1β (pg/mL) | Average IL-1Ra/IL-1β |
|---|---|---|---|
| 1 mm frit | 19192 | 328 | 94 |
| 1 mm sphere | 33653 | 1143 | 57 |
| 74 µm sphere | 24275 | 33 | 908 |
| Collagen | 22387 | 602 | 47 |
| BioCartilage ® | 12458 | 6 | 8515 |

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments. Indeed, the embodiments, examples and alternatives of the preceding paragraphs, the claims, or the following description and drawings, including any of their various aspects or respective individual features, may be practiced independently or in any combination. Features described in connection with one embodiment are applicable to all embodiments, unless such features are incompatible.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A system for preparing a serum, comprising:
   a containment device having a longitudinal axis between a proximal end having an opening and a closed distal end; the proximal end having a portion that is wider than the closed distal end;
   a cage positioned inside the portion of the proximal end that is wider than the closed distal end of said containment device, the cage having a wall or walls that extend along the longitudinal axis into the portion of the proximal end that is wider than the closed distal end, wherein the cage wall or walls include a plurality of openings, and wherein the cage comprises an open top and a floor, wherein the cage floor does not extend into the closed distal end that is narrower than the portion of the proximal end having a portion that is wider than the closed end;
   a cap attachable to said containment device and configured to cover said cage;
   an inlet port in the cap configured to introduce an autologous fluid into said containment device, wherein the inlet port is located radially outwardly of the cage relative to the longitudinal axis, such that a fluid can be injected into the containment device between an inner wall of the containment device and an outer wall of the cage; and
   an outlet port in the cap configured to remove a serum from said containment device, wherein the outlet port is located radially outwardly of the cage relative to the longitudinal axis, such that a fluid can be extracted from the containment device between an inner wall of the containment device and an outer wall of the cage.

2. The system as recited in claim 1, wherein said containment device is a test tube.

3. The system as recited in claim 1, wherein said cage is a hollow cylinder.

4. The system as recited in claim 1, comprising a tray assembly including a receptacle for receiving said containment device.

5. The system as recited in claim 4, wherein said tray assembly is configured to house at least said containment device, a needle, and a syringe.

6. The system as recited in claim 4, comprising a hand warmer packaged inside said tray assembly with said containment device.

7. The system as recited in claim 4, wherein said tray assembly includes a first housing connected to a second housing by a hinge.

8. The system as recited in claim 1, comprising a syringe connectable to said inlet port to introduce said autologous fluid into said containment device and connectable to said outlet port to remove said serum from said containment device.

9. The system as recited in claim 1, wherein said cage is removable from said containment device.

10. The system of claim 1, wherein the cage includes a plurality of legs and a slot extends between adjacent legs of the plurality of legs, wherein the legs rest at an intersection of the portion of the proximal end that is wider than the closed distal end and the closed distal end that is narrower than the proximal end.

11. The system of claim 10, wherein the plurality of legs contact an inner wall of the containment device.

12. A method for preparing a serum, comprising:
   contacting an autologous fluid to cartilage inside the containment device of the system of claim 1;
   incubating the containment device; and
   centrifuging the containment device to separate the serum from the autologous fluid.

13. The method as recited in claim 12, wherein contacting the autologous fluid to the cartilage results in the production of anabolic growth factors in the autologous fluid.

14. The method as recited in claim 12, wherein the cartilage includes allograftic cartilage, autologous cartilage, or both.

15. The method as recited in claim 12, comprising positioning the cartilage within the cage prior to contacting the autologous fluid to the cartilage.

16. The method as recited in claim 12, comprising removing the cartilage from the containment device after incubating the containment device but prior to centrifuging the containment device.

17. The method as recited in claim 16, comprising using the cartilage, which has soaked in the serum inside the containment device, to treat a subject.

18. The method as recited in claim 12, wherein incubating the containment device includes incubating the containment device within a tray assembly by activating a hand warmer.

19. The method as recited in claim 12, comprising adding a bone marrow product to the containment device after incubating the containment device.

20. The method as recited in claim 12, comprising removing waste from the protein enhanced serum using a concentrator assembly.

21. The method as recited in claim 12, comprising: extracting the serum from the containment device; and administering the serum at a point of care of a subject.

* * * * *